US007977492B2

(12) United States Patent
Yonezawa et al.

(10) Patent No.: US 7,977,492 B2
(45) Date of Patent: Jul. 12, 2011

(54) CRYSTAL OF 3-[5-[4-(CYCLOPENTYLOXY)-2-HYDROXY-BENZOYL]-2-[(3-HYDROXY-1,2-BENZI-SOXAZOL-6-YL)METHOXY]PHENYL] PROPIONIC ACID

(75) Inventors: Kenji Yonezawa, Toyama (JP); Hironori Kotsubo, Toyama (JP); Yasutaka Baba, Toyama (JP); Yukie Tada, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 370 days.

(21) Appl. No.: 12/302,375

(22) PCT Filed: May 25, 2007

(86) PCT No.: PCT/JP2007/060670
§ 371 (c)(1),
(2), (4) Date: Nov. 25, 2008

(87) PCT Pub. No.: WO2007/138996
PCT Pub. Date: Dec. 6, 2007

(65) Prior Publication Data
US 2009/0275757 A1   Nov. 5, 2009

(30) Foreign Application Priority Data
May 26, 2006   (JP) .................................. 2006-146220

(51) Int. Cl.
C07D 261/20   (2006.01)

(52) U.S. Cl. ........................................................ 548/241
(58) Field of Classification Search .................. None
See application file for complete search history.

(56) References Cited

U.S. PATENT DOCUMENTS

| 7,314,888 B1 | 1/2008 | Chaki et al. |
| 7,772,285 B2 * | 8/2010 | Chaki et al. .................. 514/679 |
| 2005/0113400 A1 | 5/2005 | Chaki et al. |

FOREIGN PATENT DOCUMENTS

| JP | 2001 328958 | 11/2001 |
| WO | 00 27792 | 5/2000 |
| WO | 03 042150 | 5/2003 |

OTHER PUBLICATIONS

U.S. Appl. No. 12/934,572, filed Sep. 24, 2010, Aikawa, et al.
U.S. Appl. No. 12/989,029, filed Oct. 21, 2010, Aikawa, et al.

* cited by examiner

*Primary Examiner* — Kamal A Saeed
(74) *Attorney, Agent, or Firm* — Oblon, Spivak, McClelland, Maier & Neustadt, L.L.P.

(57) ABSTRACT

The crystal of 3-{5-[4-(cyclopentyloxy)-2-hydroxybenzoyl]-2-[(3-hydroxy-1,2-benzisoxazol-6-yl)methoxy] phenyl}propionic acid having peaks at the position of 14.0, 16.0, 23.3, 23.7 and 26.3° and the crystal of 3-{5-[4-(cyclopentyloxy)-2-hydroxybenzoyl]-2-[(3-hydroxy-1,2-benzisoxazol-6-yl)methoxy]phenyl}propionic acid having peaks at the position of 14.6, 23.1, 24.7, 25.6 and 26.0° on 2θ of diffraction angle in a powder X-ray diffraction pattern have a small specific volume, are hard to be charged with electricity, are easily handled and are useful for an active pharmaceutical ingredient of excellent anti-rheumatic agents.

2 Claims, 3 Drawing Sheets

CRYSTAL OF 3-[5-[4-(CYCLOPENTYLOXY)-2-HYDROXYBENZOYL]-2-[(3-HYDROXY-1,2-BENZISOXAZOL-6-YL)METHOXY]PHENYL] PROPIONIC ACID

FIELD OF THE INVENTION

The present invention relates to novel crystals of 3-{5-[4-(cyclopentyloxy)-2-hydroxybenzoyl]-2-[(3-hydroxy-1,2-benzisoxazol-6-yl)methoxy]phenyl}propionic acid developed as an anti-rheumatic drug.

BACKGROUND ART

3-{5-[4-(Cyclopentyloxy)-2-hydroxybenzoyl]-2-[3-hydroxy-1,2-benzisoxazol-6-yl)methoxy]phenyl}propionic acid (hereinafter called as "T-5224") has excellent anti-arthritis action and has an osteoclastic suppressing action by arthritic activity, and have been developed as an anti-rheumatic agent (patent document 1).

In patent document 1, a manufacturing process by the crystallization of T-5224 from mixed solvents of chloroform and methanol is described.

However, the crystal of T-5224 (hereinafter called as "type I crystal") produced by this manufacturing process has following defects, (1) its specific volume is large, (2) it is easy to be charged with electricity, (3) it is not easy to be handled, (4) in the crystal, it contains chloroform and methanol which are the solvents (class 2), the amount of residue of which in a medicine should be regulated, and so forth.

Further, it is hardly to say that this manufacturing process is an industrially profitable manufacturing process because (5) waste liquid containing chloroform occurs in large quantities and environmental loads are large.

Therefore, the type I crystal cannot be satisfied as an active pharmaceutical ingredient.

[Patent document 1] international publication No. WO03/042,150 pamphlet

DISCLOSURE OF THE INVENTION

Problem to be Solved by the Invention

As an active pharmaceutical ingredient, a crystal of T-5224, which (1) has a small specific volume, (2) is hard to be charged with electricity, (3) is easily handled, (4) is produced by use of a solvent which is safe to human body, (5) is produced in the condition of low environmental loads and (6) mass production of which is possible, is strongly expected.

Means to Solve the Problem

Under these circumstances, the present inventors of the present invention have conducted intensive research zealously, as a result, found that the crystal of T-5224 having peaks at the positions of 14.0, 16.0, 23.3, 23.7 and 26.3° on 2θ of diffraction angle in powder X-ray diffraction pattern (hereinafter called as "type II crystal") and the crystal of T-5224 having peaks at the positions of 14.6, 23.1, 24.7, 25.6 and 26.0° on 2θ of diffraction angle in a powder X-ray diffraction pattern (hereinafter called as "type III crystal") are excellent as an active pharmaceutical ingredient because (1) its specific volume is small, (2) it is hard to be charged with electricity, (3) it is easy to be handled, (4) it is produced by use of a solvent which is safe to human body, (5) it is produced in the condition of low environmental loads and (6) mass production is possible, and they had completed the invention.

Effect of the Invention

The crystals of the present invention, which (1) have a small specific volume, (2) are hard to be charged with electricity, (3) are easily handled, (4) are produced by use of a solvent which is safe to human body, (5) are produced in the condition of low environmental loads, and (6) mass production of which is possible, are useful for an active pharmaceutical ingredient.

BEST MODE FOR CARRYING OUT THE INVENTION

The present invention is described in detail as follows.

The present invention relates to the type II crystal having peaks at the position of 14.0, 16.0, 23.3, 23.7 and 26.3° on 2θ of diffraction angle in a powder X-ray diffraction pattern and the type III crystal having peaks at the position of 14.6, 23.1, 24.7, 25.6 and 26.0° on 2θ of diffraction angle in a powder X-ray diffraction pattern.

These crystals of the present invention are not known at all until now, are not described in the patent document 1 at all, and are novel crystals.

In addition, characteristic peaks of powder X-ray diffraction may change by conditions of measurement.

Therefore, peaks of powder X-ray diffraction of the compounds of the present invention are not interpreted strictly.

The manufacturing process of the compounds of the present invention is explained.

The type II crystal, for example, can be produced by a manufacturing process shown as follows.

In addition, an abbreviation of "Tr" has a meaning of "triphenylmethyl" in the following.

[Manufacturing Process 1]

The type II crystal can be produced by recrystallizing the type I crystal from mixed solvents comprising one or more solvents selected from 2-propanol, butanol and acetone; water; and dimethyl sulfoxide.

A method for dissolving the type I crystal is not limited in particular, for example, (1) a method for having the type I crystal heated and dissolved in mixed solvents comprising one or more solvents selected from 2-propanol, butanol and acetone; water; and dimethyl sulfoxide, (2) a method for heating and dissolving the type I crystal in mixed solvents comprising one or more solvents selected from 2-propanol, butanol and acetone; and dimethyl sulfoxide, and adding water as keeping the dissolved state, are given.

Subsequently, the type II crystal can be produced by cooling this solution.

Seed crystal of the type II crystal may be added if necessary.

In the case that seed crystal of the type II crystal is added, temperature of addition may be the temperature of the state that the type I crystal dissolved, and may be preferably 60-65° C.

The additive amount of seed crystal is not limited in particular.

The amount of water used is preferably 7.5 to 15 times volume (v/w) as the standard of the weight of the type I crystal.

The amount of dimethyl sulfoxide used is preferably 0.3 to 0.6 times volume (v/v) as the standard of the volume of water.

The amount of one or more solvents used selected from 2-propanol, butanol and acetone is preferably within the range in which (the one or more solvents selected from 2-propanol, butanol and acetone and dimethyl sulfoxide)/(water) is 70/30 to 75/25.

In addition, the type II crystal can be produced by use of the type III crystal in stead of the type I crystal according to the method described above.

[Manufacturing Process 2]

The type II crystal can be produced by neutralization-crystallization with acid after the suspension of the type I crystal is dissolved by addition of base.

The neutralization-crystallization may be conducted by addition of seed crystal of the type II crystal if necessary.

For solvents used in this production, mixed solvents comprising ketones such as acetone and 2-butanone; and water are given.

For a base, for example, hydroxides of alkali metal or alkaline earth metal such as sodium hydroxide, potassium hydroxide, lithium hydroxide, cesium hydroxide and barium hydroxide; hydrogen carbonates of alkali metal such as sodium hydrogen carbonate and potassium hydrogen carbonate; carbonates of alkali metal or alkaline earth metal such as sodium carbonate, potassium carbonate and barium carbonate; and ammonia, and the like are given.

As a preferable base, a hydroxide of alkali metal is given, and sodium hydroxide and potassium hydroxide are more preferable.

A base can be added in solid form, but it is preferred that the base is dissolved in water and added.

For an acid, for example, a mineral acid such as hydrochloric acid, sulfuric acid, nitric acid and hydrobromic acid is given, and hydrochloric acid is preferable.

For ketones, acetone is preferable.

Sulfoxides such as dimethyl sulfoxide and amides such as N,N-dimethylformamide may be mixed as a solubilizer.

For a solubilizer, dimethyl sulfoxide is preferable.

The amount of the mixed solvents used is preferably 15 to 100 times volume (v/w) as the standard of the weight of the type I crystal, and is more preferably 15 to 30 times volume (v/w).

The ratio of mixed solvents is preferably within the range in which (ketones and solubilizer)/(water) is 60/40 to 90/10, and is more preferably within the range in which (ketones and solubilizer)/(water) is 65/35 to 75/25.

The amount of the solubilizer used is preferably within the range in which (ketones)/(solubilizer) is 100/0 to 70/30.

Temperature of neutralization is not limited in particular, but the temperature is preferably 10° C. to reflux temperature, and is more preferably 10-60° C.

In the case that seed crystal of the type II crystal is added, it is preferable to add to liquid of pH 6.0 to 7.5.

The additive amount of seed crystal is not limited in particular.

In addition, the type II crystal can be produced by use of the type III crystal in stead of the type I crystal according to the method described above.

[Manufacturing Process 3]

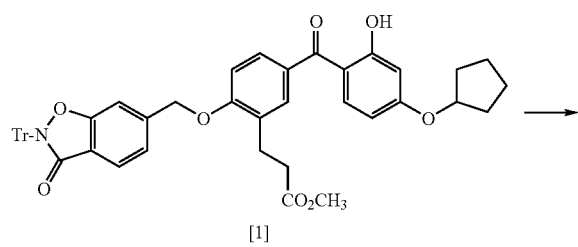

[1]

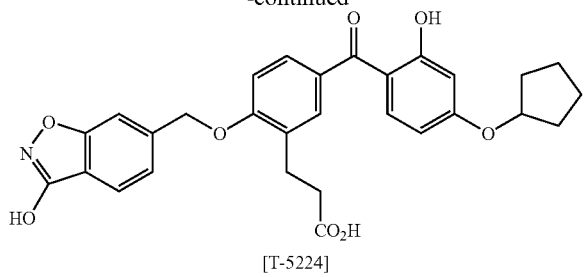

[T-5224]

After the compound of formula [1] is subjected to deprotection reaction, the type II crystal can be produced by adding base to the reaction mixture to dissolve T-5224, and subsequently by neutralizing and crystallizing with acid.

The neutralization-crystallization may be conducted by addition of seed crystal of the type II crystal if necessary.

Deprotection reaction may be conducted by the method, for example, described in Protective Groups In Organic Synthesis, T. W. Greene, John Wiley & Sons INC., 1999, the third edition, p. 369-387, 583-584 and the like method.

For solvents used in this reaction, mixed solvents comprising ketones such as acetone and 2-butanone; and water, are given.

Sulfoxides such as dimethyl sulfoxide and amides such as N,N-dimethylformamide may be mixed as a solubilizer.

For a solubilizer, dimethyl sulfoxide is preferable.

Addition of base and neutralization-crystallization may be conducted according to the manufacturing process 2.

The type III crystal, for example, can be produced by a manufacturing process shown as follows.

[Manufacturing Process 4]

After the suspension of the type I crystal was dissolved by addition of base, the type III crystal can be produced by neutralization-crystallization with acid and subsequent heating and stirring.

The neutralization-crystallization may be conducted by addition of seed crystal of the type III crystal if necessary.

For the solvent used in this production, mixed solvents comprising one or more solvents selected from ethyl acetate, butyl acetate and 4-methyl-2-pentanone; one or more solvents selected from acetone and 2-butanone; and water are given.

For a base, for example, hydroxides of alkali metal or alkaline earth metal such as sodium hydroxide, potassium hydroxide, lithium hydroxide, cesium hydroxide and barium hydroxide; hydrogen carbonates of alkali metal such as sodium hydrogen carbonate and potassium hydrogen carbonate; carbonates of alkali metal or alkaline earth metal such as sodium carbonate, potassium carbonate and barium carbonate; and ammonia are given.

For a preferable base, hydroxide of alkali metal is given, and sodium hydroxide and potassium hydroxide are more preferable.

A base can be added in solid form, but it is preferred that the base is dissolved in water and added.

For an acid, for example, a mineral acid such as hydrochloric acid, sulfuric acid, nitric acid and hydrobromic acid is given, and hydrochloric acid is preferable.

The amount of one or more solvents used selected from ethyl acetate, butyl acetate and 4-methyl-2-pentanone is preferably 5 to 10 times volume (v/w) as the standard of the weight of the type I crystal.

The amount of one or more solvents used selected from acetone and 2-butanone is preferably 0.5 to 1.0 times volume (v/v) as the standard of the volume of one or more solvents selected from ethyl acetate, butyl acetate and 4-methyl-2-pentanone.

The amount water used is preferably 0.5 to 2.0 times volume (v/v) as the standard of the volume of one or more solvents selected from ethyl acetate, butyl acetate and 4-methyl-2-pentanone.

Temperature of neutralization is not limited in particular, but the temperature is preferably 10° C. to reflux temperature, and is more preferably 10-60° C.

In the case that seed crystal of the type III crystal is added, it is preferable to add to liquid of pH 6.0 to 7.5.

The additive amount of seed crystal is not limited in particular.

The high-purity type III crystal can be produced by stirring at equal to or more than 50° C. for equal to or more than 1 hour, preferably by stirring at 50-70° C. for equal to or more than 1 hour, and more preferably by stirring at 50-70° C. for 1 to 3 hours after neutralization-crystallization.

In addition, the type III crystal can be produced by use of the type II crystal in stead of the type I crystal according to the method described above.

[Manufacturing Process 5]

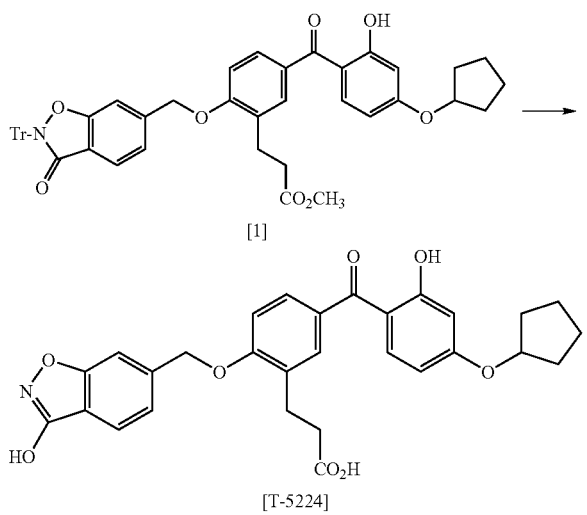

After the compound of formula [1] was subjected to deprotection reaction, the type III crystal can be produced by adding base to the reaction mixture to dissolve T-5224, subsequently by neutralizing and crystallizing with acid, and subsequently by heating and stirring.

The neutralization-crystallization may be conducted by addition of seed crystal of the type III crystal if necessary.

Deprotection reaction may be conducted according to the manufacturing process 3.

For the solvent used in this reaction, mixed solvents comprising one or more solvents selected from ethyl acetate, butyl acetate and 4-methyl-2-pentanone; one or more solvents selected from acetone and 2-butanone; and water are given.

Addition of base, neutralization-crystallization and heating-stirring may be conducted according to the manufacturing process 4.

In the case that the compounds of the present invention (the type II crystal and the type III crystal) are used as a medicine, they can be used alone or mixed.

In addition, the compound of the present invention, for example, may be mixed with pharmaceutical auxiliaries such as an excipient, a carrier, and a diluent, used for formulation.

These can be administered by orally or parenterally in the forms such as tablets, capsules, powders, syrups, granules, pills, suspensions, emulsions, liquids, fine particles, suppositories or ointments according to conventional methods.

Even more particularly, the present invention compound is mixed with the type I crystal, and it may be used.

Next, utility of the compound of the present invention is explained with the following tests.

Test Example 1

Measurement of Specific Volume

Test materials were the compound of the present invention (the type II crystal and the type III crystal) and the type I crystal.

After 3.0 g of the test material was put in a measuring cylinder and the measuring cylinder was shaken for 1 minute, the volume was measured. Furthermore, after the measuring cylinder was shaken for 1 minute until the volume of the test material did not decrease, the procedure of measuring the volume was repeated. The volume of the test material is measured, and the specific volume was calculated. The results are shown in Table 1.

TABLE 1

| crystal form | specific volume (cm$^3$/g) |
| --- | --- |
| type I crystal | 5.0 |
| type II crystal | 1.3 |
| type III crystal | 2.5 |

The specific volume of the compounds of the present invention (the type II crystal and the type III crystal) was small in comparison with it of the type I crystal.

Test Example 2

The Amount of Electrostatic Charge

Test materials were the compounds of the present invention (the type II crystal and the type III crystal) and the type I crystal.

20 g of the test material was put on a paper, and the electric potential of charge was measured. Measurement was conducted 3 times, and the average-value was to be the electric potential of charge. The results are shown in Table 2.

Measuring instrument: electrostatic measuring instrument FMX-003 (Simucojapan Co., Ltd.)
Measurement distance: 25 mm

TABLE 2

| crystal form | electric potential of charge (V) |
| --- | --- |
| type I crystal | −3270 |
| type II crystal | +30 |
| type III crystal | −560 |

The amount of electrostatic charge of the compounds of the present invention (the type II crystal and the type III crystal) was small in comparison with it of the type I crystal, and was hard to be charged with static electricity.

Next, the present invention is explained with examples and manufacturing examples, but the present invention is not limited thereto.

Condition of measurement for powder X-ray diffraction anti-cathode: Cu, tube voltage: 40 kV, tube current: 20 mA

Example 1

Production of the Type II Crystal (1)

6.0 mL of dimethyl sulfoxide, 10 mL of water and 20 mL of acetone were added to 1.00 g of the type I crystal, and it was heated and dissolved. After cooling, the crystal which separated out was filtrated and collected, and air-dried to give 0.85 g of the type II crystal.

The powder X-ray diffraction data were shown in Table 3, and the pattern was shown in FIG. 1.

IR(ATR): 1,704 cm$^{-1}$

TABLE 3

| 2θ | d | relative intensity |
|---|---|---|
| 5.5000 | 16.0539 | 17.4 |
| 11.0800 | 7.9789 | 30.2 |
| 13.9800 | 6.3295 | 70.3 |
| 16.0400 | 5.5209 | 52.0 |
| 17.1200 | 5.1752 | 42.2 |
| 18.4800 | 4.7971 | 18.9 |
| 19.2600 | 4.6047 | 27.6 |
| 19.8000 | 4.4803 | 49.3 |
| 20.8800 | 4.2508 | 18.6 |
| 22.1600 | 4.0082 | 39.3 |
| 23.2600 | 3.8210 | 89.4 |
| 23.6800 | 3.7542 | 100.0 |
| 26.3400 | 3.3808 | 68.5 |
| 28.4000 | 3.1400 | 32.4 |
| 29.8600 | 2.9898 | 21.3 |

Example 2

Production of the Type II Crystal (2)

12 mL of dimethyl sulfoxide and 40 mL of acetone were added to 2.00 g of the type I crystal, and it was dissolved. 20 mL of water was added dropwise at 60-61° C., after cooling, the crystal which separated out was filtrated and collected, and air-dried to give 1.66 g of the type II crystal. The powder X-ray diffraction pattern accorded with the example 1.

IR(ATR): 1,703 cm$^{-1}$

Example 3

Production of the Type II Crystal (3)

0.50 g of the type I crystal was added to 2.0 mL of dimethyl sulfoxide, 8.0 mL of acetone and 5.0 mL of water, and 0.40 mL of 20% sodium hydroxide aqueous solution was added, and it was dissolved. It was heated to 40° C., and 0.45 mL of 6 mol/L hydrochloric acid was added dropwise. After cooling, the crystal which separated out was filtrated and collected, and air-dried to give 0.47 g of the type II crystal.

The powder X-ray diffraction pattern accorded with the example 1.

IR(ATR): 1,703 cm$^{-1}$

Example 4

Production of the Type III Crystal (1)

0.50 g of the type I crystal was added to 5.0 mL of butyl acetate, 2.5 mL of acetone and 5.0 mL of water, and 0.43 mL of 20% sodium hydroxide aqueous solution was added, and it was dissolved. 0.37 mL of 6 mol/L hydrochloric acid was added dropwise, it was heated to 50° C., and stirred for 2.5 hours. After cooling, the crystal which separated out was filtrated and collected, and air-dried to give 0.45 g of the type III crystal.

The powder X-ray diffraction data were shown in Table 4, and the pattern was shown in FIG. 2.

IR(ATR): 1,743 cm$^{-1}$

TABLE 4

| 2θ | d | relative intensity |
|---|---|---|
| 13.6000 | 6.5053 | 68.5 |
| 14.6000 | 6.0621 | 93.6 |
| 15.5000 | 5.7120 | 40.4 |
| 15.8600 | 5.5832 | 70.2 |
| 17.1400 | 5.1690 | 73.4 |
| 21.0000 | 4.2269 | 57.3 |
| 21.5000 | 4.1297 | 47.6 |
| 21.9000 | 4.0552 | 31.8 |
| 23.0600 | 3.8537 | 95.6 |
| 23.8800 | 3.7232 | 83.8 |
| 24.7399 | 3.5957 | 94.7 |
| 25.5600 | 3.4821 | 100.0 |
| 26.0200 | 3.4216 | 87.9 |
| 26.8600 | 3.3165 | 56.4 |
| 28.6000 | 3.1186 | 49.9 |

Preparation 1

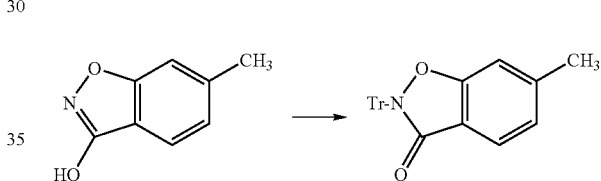

20.0 g of 6-methyl-1,2-benzisoxazol-3-ol, 9.93 g of pyridine and 35.0 g of triphenylmethyl chloride were added to 100 mL of methylene chloride, and this was stirred for 1 hour at 35-45° C. 40 mL of water and 24 mL of 20% sodium hydroxide aqueous solution were added to the reaction mixture, and the organic layer was separated. The aqueous layer was extracted with 20 mL of methylene chloride, and the organic layers were combined, and 70 mL of the solvent was distilled off under atmospheric pressure, and 100 mL of 2-propanol was added, and 40 mL of the solvent was distilled off under atmospheric pressure. 40 mL of water was added to the reaction mixture, and after stirring for 30 minutes at 10-25° C., the solid was filtered and collected, and 46.0 g of a light yellow solid of 6-methyl-2-triphenylmethyl-1,2-benzisoxazol-3(2H)-one was obtained.

$^{1}$H-NMR (DMSO-d$_6$) δ value:

2.36 (3H, s), 7.03 (1H, d, J=8.0 Hz), 7.18-7.33 (10H, m), 7.43-7.47 (7H, m)

Preparation 2

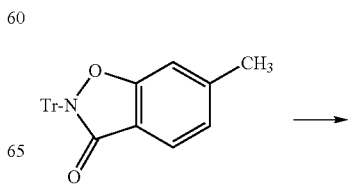

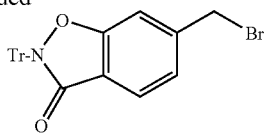

24.0 kg of 6-methyl-2-triphenylmethyl-1,2-benzisoxazol-3(2H)-one and 18.6 kg of N-bromosuccinimide were added to 48 L of chlorobenzene. A solution of 0.30 kg of 2,2'-azobis (2,4-dimethylvaleronitrile) in 4.8 L of methylene chloride was added dropwise 5 times every 1 hour at 70-80° C. After completing the instillation, this was stirred for 1 hour at the same temperature. 96 L of methylene chloride, 2.40 kg of celite, 24 L of 20% sodium hydroxide aqueous solution, 0.77 kg of sodium sulfite and 48 L of water were added to the reaction mixture. The insoluble matter was filtered off, and the cake was washed with 72 L of methylene chloride. The filtrate and washing solution were combined, and the organic layer was separated. 24 L of methylene chloride, 12.7 kg of potassium carbonate and 6.07 kg of phosphonic acid dimethyl ester were added to the organic layer, and this was stirred for 4 hours at 40-50° C. 48 L of water and 14 L of 20% sodium hydroxide aqueous solution were added to the reaction mixture, and the organic layer was separated. The aqueous layer was extracted with 24 L of methylene chloride, and the organic layers were combined, and 24 L of methylene chloride was added, and 210 L of the solvent was distilled off under atmospheric pressure. 24 L of acetone was added to the reaction mixture, and 40 L of the solvent was distilled off under atmospheric pressure. 96 L of 2-propanol and 24 L of water was added dropwise, and the solid was filtered and collected, and 25.2 kg of a white solid of 6-(bromomethyl)-2-triphenylmethyl-1,2-benzisoxazol-3(2H)-one was obtained.

$^1$H-NMR (DMSO-$d_6$) δ value:
4.72 (2H, s), 7.22-7.34 (10H, m), 7.44-7.49 (7H, m), 7.58 (1H, d, J=8.0 Hz)

Preparation 3

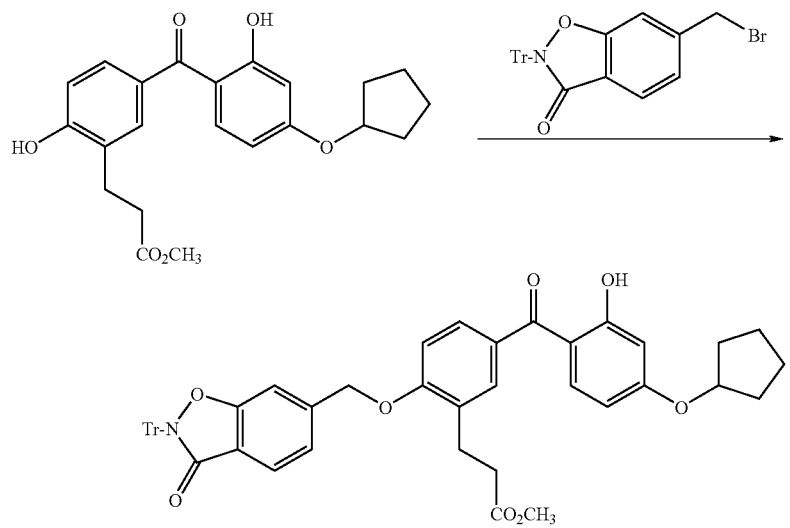

12.5 kg of 3-{5-[4-(cyclopentyloxy)-2-hydroxybenzoyl]-2-hydroxyphenyl}propionic acid methyl ester, 15.6 kg of 6-(bromomethyl)-2-triphenylmethyl-1,2-benzisoxazol-3(2H)-one and 4.49 kg of potassium carbonate were added to 125 L of acetone. This was stirred for 5 hours under heating reflux. After cooling the reaction mixture, 29 L of water was added, 2.9 L of hydrochloric acid was added dropwise, and solids were filtered. This resulted in 19.7 kg of 3-{5-[4-(cyclopentyloxy)-2-hydroxybenzoyl]-2-[(3-oxo-2-triphenylmethyl-2,3-dihydro-1,2-benzisoxazol-6-yl)methoxy]phenyl}propionic acid methyl ester in the form of a light yellowish-white solid.

$^1$H-NMR (DMSO-$d_6$) δ value:
1.55-1.78 (6H, m), 1.90-2.00 (2H, m), 2.63 (2H, t, J=7.6 Hz), 2.93 (2H, t, J=7.6 Hz), 3.49 (3H, s), 4.88-4.94 (1H, m), 5.33 (2H, s), 6.46-6.51 (2H, m), 7.13 (1H, d, J=8.3 Hz), 7.22-7.25 (3H, m), 7.30-7.34 (7H, m), 7.42-7.56 (10H, m), 7.63 (1H, d, J=8.0 Hz), 12.00 (1H, s)

Preparation 4

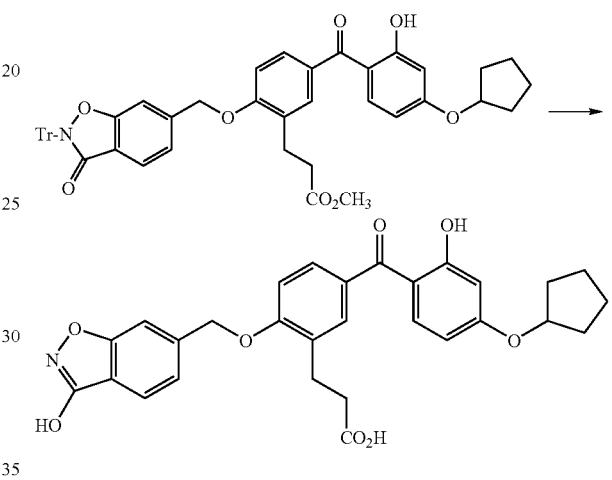

(1) 100 g of 3-{5-[4-(cyclopentyloxy)-2-hydroxybenzoyl]-2-[(3-oxo-2-triphenylmethyl-2,3-dihydro-1,2-benzisoxazol-6-yl)methoxy]phenyl}propionic acid methyl ester was suspended in 500 mL of acetone, and 240 mL of water and 60 mL of water of 15.5 g of sodium hydroxide were added, it was stirred at 20-30° C. for 2 hour and was stirred at 5-15° C. for 1 hour, and then the solid was filtrated and collected to give 146 g of a yellow solid.

(2) 146 g of the yellow solid was suspended in a mixed solution of 130 mL of 4-methyl-2-pentanone and 300 mL of acetone, and subsequently 50 mL of hydrochloric acid and 25 mL of water were added dropwise, and it was stirred at 45-55° C. for 2 hours.

After 40 mL of 4-methyl-2-pentanone, 130 mL of water, 90 mL of dimethyl sulfoxide and 117 mL of 20% sodium hydroxide aqueous solution were added to the reaction mixture, 13 mL of hydrochloric acid was added dropwise at 45-55° C. The aqueous layer was separated and collected, 100 mL of acetone was added, the insoluble matter was filtrated, and the residue was washed with a mixture of 120 mL of acetone and 80 mL of water, subsequently washed with 200 mL of acetone. The filtrate and the washings were combined, and 21 mL of acetone was added. Seed crystal of the type II crystal was added at 45-55° C., 50 mL of dimethyl sulfoxide solution of 29 mL of hydrochloric acid was added dropwise at the same temperature, subsequently it was stirred at 5-15° C. for 1 hour, and the solid was filtrated and collected to give the type II crystal 59.0 g of a light yellow.

The powder X-ray diffraction pattern accorded with the example 1.

IR(ATR): 1,704 cm$^{-1}$

Preparation 5

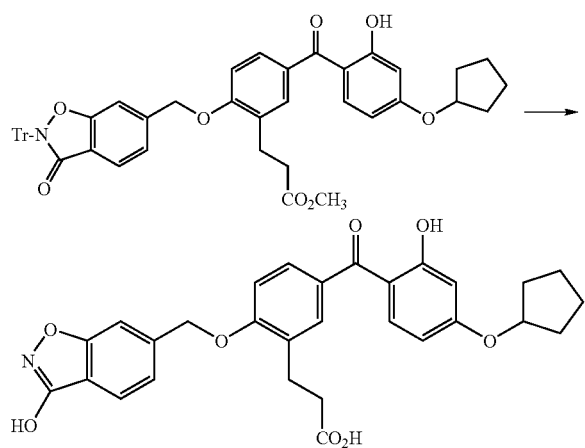

(1) 270 g of 3-{5-[4-(cyclopentyloxy)-2-hydroxybenzoyl]-2-[(3-oxo-2-triphenylmethyl-2,3-dihydro-1,2-benzisoxazol-6-yl)methoxy]phenyl}propionic acid methyl ester was suspended in 1.35 L of acetone, and 540 mL of water and 270 mL of water of 41.9 g of sodium hydroxide were added, it was stirred at 25-35° C. for 3 hours and was stirred at 5-15° C. for 30 minutes, and the solid was filtrated and collected to give 315 g of a yellow solid.

(2) 5.84 g of the yellow solid was suspended in a mixed solution of 10 mL of 4-methyl-2-pentanone, 10 mL of 2-butanone and 1.5 mL of water, subsequently 2.5 mL of hydrochloric acid was added dropwise, and it was stirred at 45-55° C. for 3 hours. 15 mL of water and 7 mL of 20% sodium hydroxide aqueous solution were added to the reaction mixture, and it was stirred at 30-40° C. The aqueous layer was separated and collected, 7.5 mL of water, 20 mL of 4-methyl-2-pentanone, 10 mL of 2-butanone and 0.7 mL of hydrochloric acid were added, subsequently 1 mL of hydrochloric acid and seed crystal of the type III crystal were added at 60-70° C., and 1 mL of hydrochloric acid was added dropwise and it was stirred at 60-70° C. for 2 hours. The organic layer was separated and collected, 5 mL of acetone was added, subsequently it was stirred at 20-25° C. for 30 minutes, and the solid was filtrated and collected to give the type III crystal 2.95 g of a light yellow.

The powder X-ray diffraction pattern accorded with the example 4.

IR(ATR): 1,743 cm$^{-1}$

Reference Example 1

In the manner described in example 35 of international publication No. 03/042,150 pamphlet, the type I crystal was produced.

The powder X-ray diffraction pattern is shown in FIG. 3.

INDUSTRIAL APPLICABILITY

Figure 1:
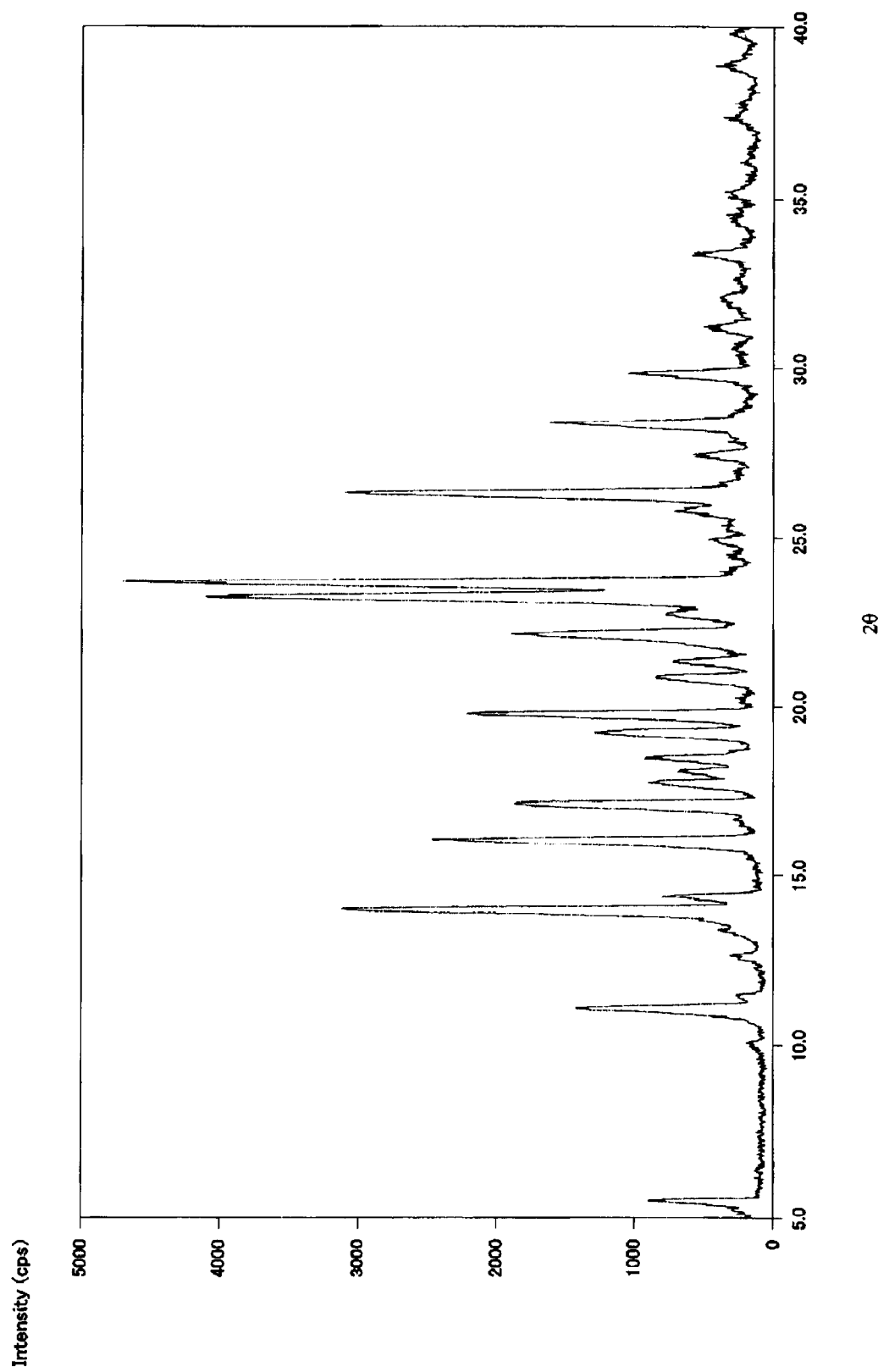
FIG. 1 represents the powder X-ray diffraction pattern of the type II crystal (the ordinate represents Intensity (cps)); the abscissa represents an angle of diffraction (2θ(°)).
Figure 2:
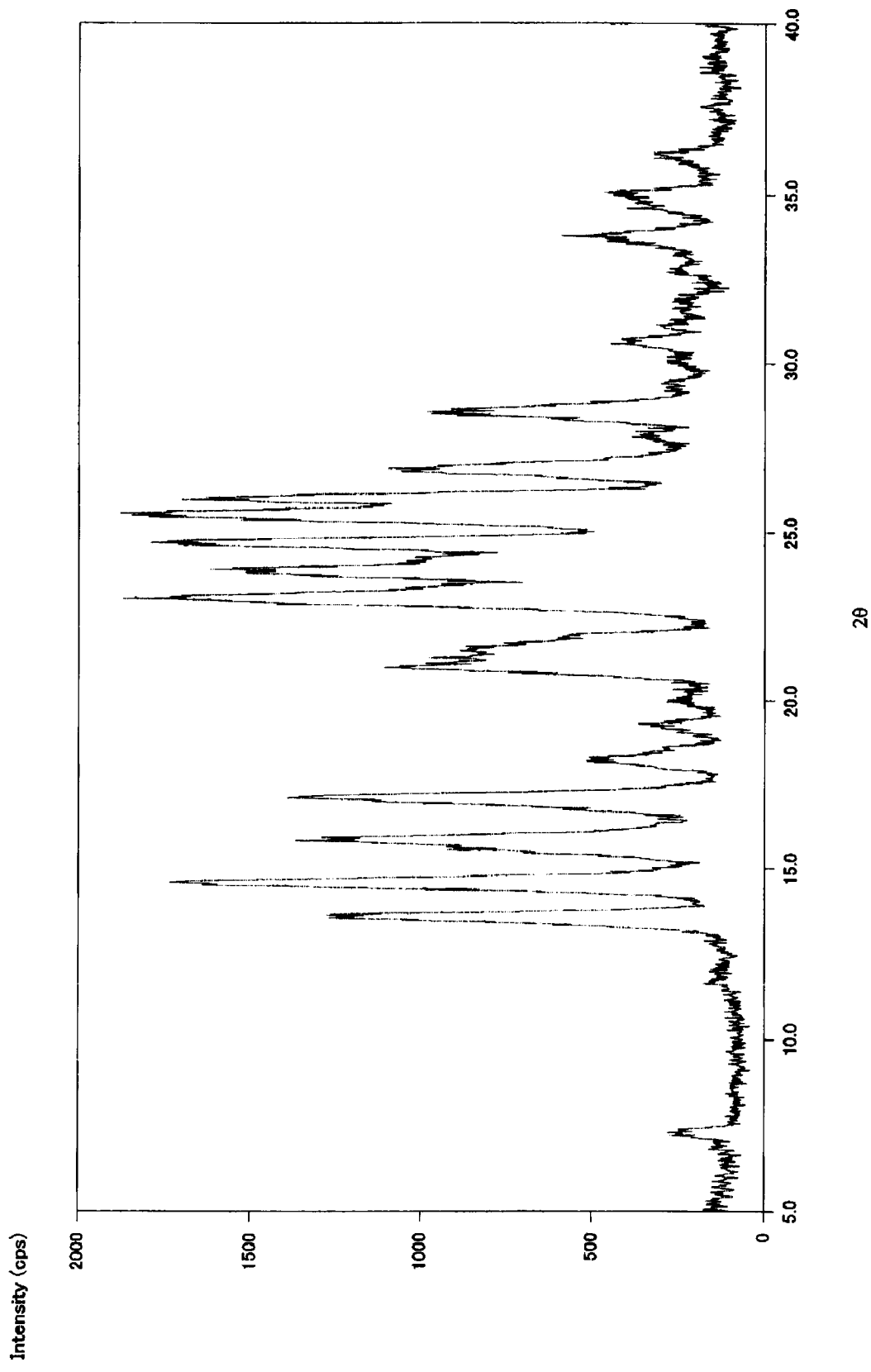
FIG. 2 represents the powder X-ray diffraction pattern of the type III crystal (the ordinate represents Intensity (cps)); the abscissa represents an angle of diffraction (2θ(°)).
Figure 3:
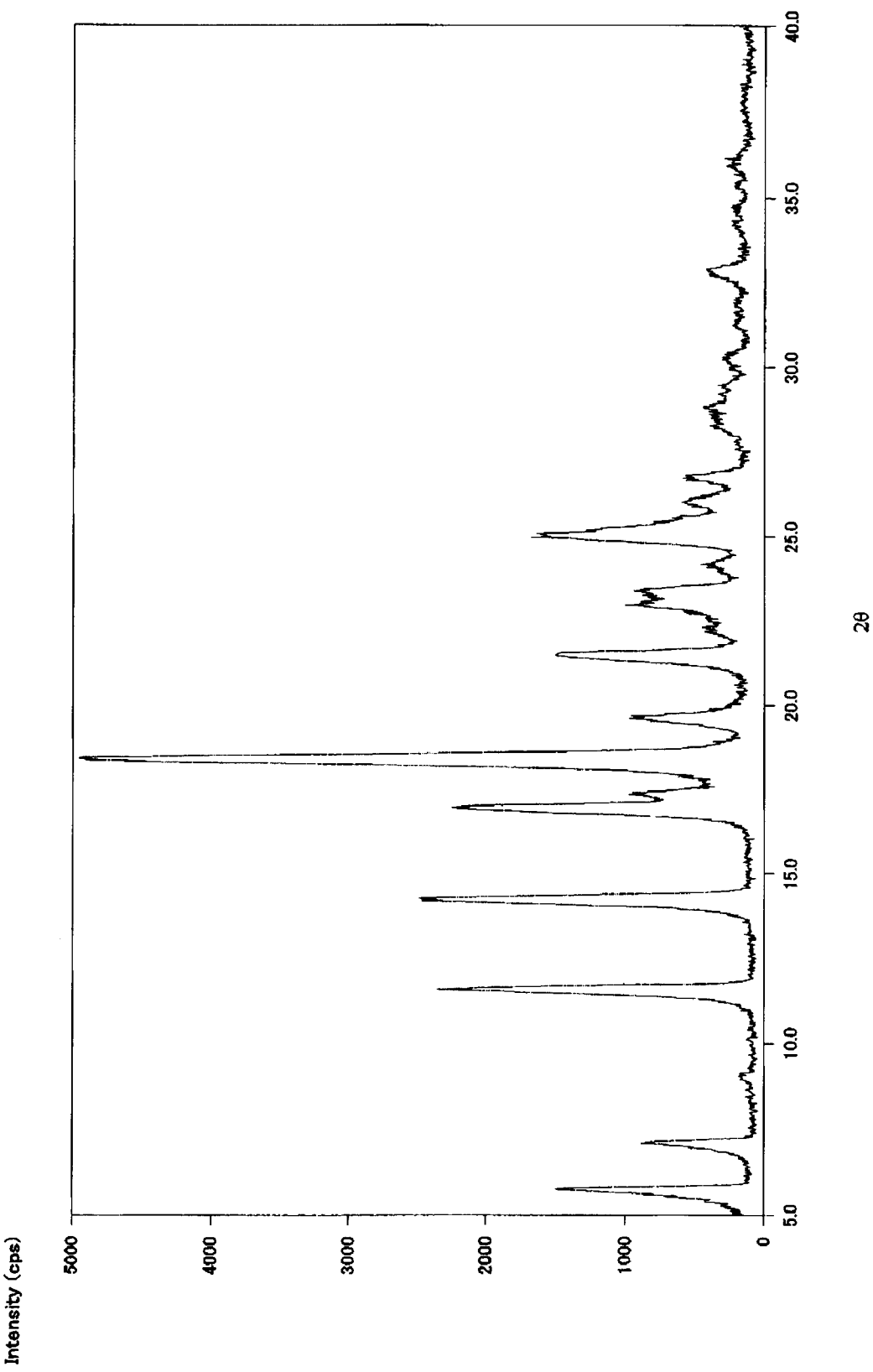
FIG. 3 represents the powder X-ray diffraction pattern of the type I crystal (the ordinate is Intensity (cps)); the abscissa represents an angle of diffraction (2θ(°)).

The crystal of the present invention, (1) has a small specific volume, (2) is hard to be charged with electricity, (3) is easily handled, (4) is produced by use of a solvent which is safe to human body, (5) is produced in the condition of low environmental loads, and (6) mass production of which is possible, is useful for an active pharmaceutical ingredient.

The invention claimed is:

1. The crystal of 3-{5-[4-(cyclopentyloxy)-2-hydroxybenzoyl]-2-[(3-hydroxy-1,2-benzisoxazol-6-yl)methoxy]phenyl}propionic acid having peaks at the position of 14.0, 16.0, 23.3, 23.7 and 26.3° on 2θ of diffraction angle in a powder X-ray diffraction pattern.

2. The crystal of 3-{5-[4-(cyclopentyloxy)-2-hydroxybenzoyl]-2-[(3-hydroxy-1,2-benzisoxazol-6-yl)methoxy]phenyl}propionic acid having peaks at the position of 14.6, 23.1, 24.7, 25.6 and 26.0° on 2θ of diffraction angle in a powder X-ray diffraction pattern.

* * * * *